United States Patent [19]

Hall et al.

[11] Patent Number: 5,476,615
[45] Date of Patent: Dec. 19, 1995

[54] LOW FOAM SANITIZERS

[75] Inventors: Larry K. Hall, Nazareth, Pa.; Michael Y. Chiang, Flemington, N.J.

[73] Assignee: Lonza Inc., Fair Lawn, N.J.

[21] Appl. No.: 246,683

[22] Filed: May 20, 1994

[51] Int. Cl.⁶ .............................. C11D 1/62; C11D 1/75; C11D 1/835; A61L 2/18
[52] U.S. Cl. ........................ 252/547; 252/106; 422/1; 134/22.1
[58] Field of Search ............................. 564/297, 291; 422/1; 252/106, 547; 134/22.1

[56] References Cited

U.S. PATENT DOCUMENTS

| | | | |
|---|---|---|---|
| 3,336,387 | 8/1967 | Finch et al. | 564/297 |
| 3,389,178 | 6/1968 | Fields et al. | 564/297 |
| 3,484,523 | 12/1969 | Findlan et al. | 424/248 |
| 3,754,033 | 8/1973 | Shay et al. | 260/567.6 M |
| 4,113,631 | 9/1978 | Thompson | 252/8.55 C |
| 4,229,313 | 10/1980 | Joy | 252/547 |
| 4,259,217 | 3/1981 | Murphy | 252/547 |
| 4,264,479 | 4/1981 | Flanagan | 252/524 |
| 4,425,243 | 1/1984 | Green et al. | 252/8.5 C |
| 4,450,174 | 5/1984 | Green et al. | 424/329 |
| 4,576,728 | 3/1986 | Stoddart | 252/547 |
| 4,650,904 | 3/1987 | Fujita | 564/298 |
| 4,659,565 | 4/1987 | Smith et al. | 564/297 |
| 4,783,283 | 11/1988 | Stoddart | 252/547 |
| 4,921,627 | 5/1990 | Copeland et al. | 252/99 |
| 4,938,893 | 7/1990 | Copeland et al. | 252/527 |
| 5,000,867 | 3/1991 | Heinhuis-Walther et al. | 252/547 |
| 5,078,896 | 1/1992 | Rorig et al. | 252/547 |

FOREIGN PATENT DOCUMENTS

| | | |
|---|---|---|
| 0747963 | 12/1966 | Canada . |
| 0267662A2 | 5/1988 | European Pat. Off. .......... C11D 1/75 |
| WO92/13934 | 8/1992 | European Pat. Off. ........ C11D 1/835 |
| 1567214 | 4/1969 | France . |

OTHER PUBLICATIONS

Ralston, A. W., (Mar. 1948), *J. Org. Chem.*, 13:186.

*Primary Examiner*—Paul Lieberman
*Assistant Examiner*—Erin Harriman
*Attorney, Agent, or Firm*—Darby & Darby

[57] ABSTRACT

A sanitizer composition comprising
a) an amine oxide having the formula:

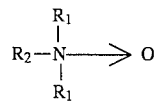

wherein the $R_1$ groups are independently selected from $C_1$–$C_4$ alkyl or alkoxy groups and $R_2$ is a branched chain $C_{11}$–$C_{16}$ alkyl group, and b) a quaternary ammonium compound having the formula:

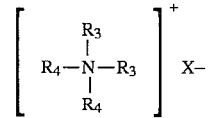

wherein the $R_3$ groups are independently selected from $C_1$–$C_4$ alkyl or alkoxy groups and the $R_4$ groups are $C_8$–$C_{16}$ linear or branched alkyl groups wherein at least one of the $R_4$ groups is a branched $C_8$–$C_{16}$ alkyl group, and X is chloride, bromide, iodide, carbonate or alkylcarboxylate having a $C_1$–$C_{18}$ alkyl radical, and the use thereof.

13 Claims, No Drawings

LOW FOAM SANITIZERS

BACKGROUND OF THE INVENTION

Sanitizers and disinfectants are formulations intended to reduce or destroy pathogenic bacteria, fungi and viruses. Quaternary ammonium compounds serve as the active antimicrobial agent in the majority of sanitizers currently used in Industrial and Institutional (I&I) applications. In addition to an antimicrobial agent, most contain co-surfactants to assist in solubilizing soil particulates, as well as chelating agents to overcome deficiencies with hard water, and builders or acids to aid in cleaning performance.

A specialized category of sanitizers and disinfectants is directed towards clean-in-place (CIP) applications. Examples of CIP applications include cleaning of dairy and brewery tanks and meat packing plants and parts. Unlike typical hard surface cleaning where high, stable foaming formulations are used, CIP applications normally demand low, fast breaking foams to avoid overflow, product loss, pump cavitation, and streaks and films on treated surfaces after drying.

Low foam sanitizing solutions are also needed for machine-applied disinfectant/cleaners. Maintenance workers use modern formulations that combine antimicrobials with surfactants to both clean and disinfect in one step. When the formulations are applied by machine, however, there is often excessive foam generation due to the high turbulence at the brush/floor interface. The resulting higher foam can lead to streaks when the floor dries and leave unsightly residue in heavily trafficked areas.

Two types of quaternary ammonium compounds are typically used to impart antimicrobial activity to household and I&I formulations. These are alkyldimethylbenzylammonium chlorides (ADBACs) and dialkyldimethylammonium chlorides (DDACs). Both of these classes of compounds are excellent surface active agents; however, the high, stable foams they develop are disadvantageous in CIP applications.

A possible solution to this problem is to include low-foaming co-surfactants in the formulations. The foam building properties of ADBACs and DDACs, however, are so potent as to overcome the normally low foaming characteristics of such co-surfactants.

A limiting consideration in the search for an appropriate co-surfactant is that many standard surfactants such as anionic sulfates, ether sulfates, or sulfonates cannot be used in quaternary ammonium-based formulations, since they form precipitates and produce hazy, two phase systems with reduced antimicrobial efficacy. Thus, co-surfactants in these formulations are normally limited to nonionics.

Another goal in using surfactants in sanitizer formulations is to reduce the surface tension of the water in the cleaning vessel, thereby improving wetting, enhancing dirt and soil removal and improving drainage of the cleaning solution. Unfortunately, most surfactants that a) are compatible with quaternary ammonium-based compounds, and, b) display low foam characteristics, have limited surface tension reduction properties at the levels employed.

One approach to reducing the foaming tendencies of disinfectant and cleaner solutions is to include silicone in the formulations. Silicones, however, tend to accumulate on surfaces, leaving residues on vessel walls and pipe linings that often become problematic in later processing stages as well as in coating and painting steps. Also, silicones are not readily biodegradable and accumulate in the biosphere, leading many CIP formulators to reject them out of hand.

Therefore, there is a need in the art for formulations that are effective in disinfecting and cleansing and possess foaming properties compatible with CIP and machine-cleaning applications. U.S. Pat. No. 4,938,893 (hereinafter the "'893 patent") discloses $C_{1-4}$ alkyl-di $C_{6-20}$ alkyl amine oxide compounds that are used in combination with a hardness sequestering agent, a source of alkalinity, and an anionic surfactant, to produce a detersive solution with low-foaming properties. Nevertheless, the formulations of the '893 patent produce too much foam for CIP and machine-applied cleaning applications. In addition, this invention is restricted to detersive applications which do not present the difficulties presented by sanitizer systems.

BRIEF DESCRIPTION OF THE INVENTION

It has now been found that, sanitizing formulations containing selected amine oxides and quaternary ammonium compounds produce much less foam than those heretofore known in the art. The formulations of the present invention are antimicrobial, have excellent wetting characteristics, do not precipitate at ambient and low temperatures, can be formulated with a wide range of builders and chelating agents, and produce solutions with low surface tension for superior wetting characteristics. In addition, these formulations do not require silicones or other foam control agents and are readily biodegradable at use concentrations employed.

Accordingly, it is an object of this invention to provide unique amine oxides, particularly isododecyldimethylamine oxide, in combination with quaternary ammonium compounds, particularly decylnonyl and decylisononyldimethyl ammonium chlorides, for use as disinfectant cleaners and sanitizers.

A further object of the invention is to provide safe, effective combinations of amine oxide and quaternary ammonium compounds that produce extremely fast-breaking foam when added to a circulating body of water, Such formulations are especially useful in CIP and machine cleaning applications where foam production is undesirable.

These and other objects of the invention will be apparent to those of ordinary skill in the art in light of the detailed description below.

DETAILED DESCRIPTION OF TEE INVENTION

The present invention is based upon the unexpected discovery that the combination of certain branched alkyl chain amine oxides with certain branched dialkyl quaternary ammonium compounds produces formulations that exhibit low surface tension, fast wetting time and, most importantly, minimal amounts of foam with fast-breaking properties. These products can be used in low foaming sanitizing compositions and/or low foaming disinfectant cleaners.

The co-surfactants of the present invention are amine oxides having the following structure:

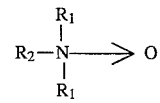

wherein the $R_1$ groups are independently selected from $C_1$–$C_4$ alkyl or alkoxy groups, and $R_2$ is a branched $C_{11}$–$C_{16}$ alkyl chain group. For $R_1$, methyl, ethyl, and hydroxyethyl are preferred and methyl is most preferred. For $R_2$, the branched $C_{12}$, and $C_{13}$ are preferred.

Specific examples of the preferred amine oxide surfactants for use in the novel formulations of the present invention include isononyldimethylamine oxide, isododecyldimethylamine oxide and isotridecyldimethylamine oxide.

The amine oxides of the present invention can be synthesized by well known methods. A particularly preferred amine oxide is prepared using a branched alcohol having a typical chain length distribution of 6% $C_{10}$, 18% $C_{11}$, 55% $C_{12}$, 20% $C_{13}$, and 1% $C_{14}$ (the major isomer is trimethyl-1-nonanol.) Preparation of the amine oxides described herein is disclosed in co-pending U.S. patent application by C.-I. Tseng, entitled "Low Foam Branched Alkyldimethylamine Oxides", filed on even date herewith, which is hereby incorporated by reference in its entirety.

The dialkyldimethyl quaternary ammonium compounds of the present invention have the following structure:

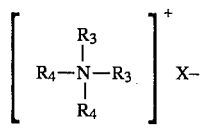

wherein the $R_3$ groups are independently selected from $C_1$–$C_4$ alkyl or alkoxy groups; the $R_4$ groups are independently selected from $C_8$ to $C_{16}$ straight-chain or branched groups, wherein at least one must be a branched chain such as 2-ethylhexyl, isooctyl, isodecyl, or isononyl; and X is an anion such as chloride, bromide, iodide, carbonate and alkyl carboxylate having a $C_1$–$C_{18}$ alkyl radical.

Specific examples of preferred quaternary ammonium compounds of the present invention include:

decylisodecyldimethylammonium chloride decylisononyldimethylammonium chloride isodecylnonyldimethylammonium chloride diisodecyldimethylammonium chloride These quaternaries may be prepared by any known process. See, for example, U.S. Pat. Nos. 3,754,033 and 4,450,174 as well as A. W. Ralston, et al., J. Org. Chem., Vol. 13, p. 186 (1948), which are incorporated herein by reference.

The final formulations can also include chelators such as ethylenediaminetetraacetic acid (EDTA), sodium hydroxide for pH regulation, and dyes and fragrances such as those commonly used in the art in cleaning and disinfecting solutions.

For use in a sanitizing system, the amine oxides and quaternary ammonium compounds listed above can be blended in a ratio that varies from about 10:1 to about 0.1:1 on a 100% active basis. Formulations useful in the present invention are listed in Table A:

are described below:

Equilibrium and Dynamic Surface Tension Measurements

These measurements were conducted with the SensaDyne Surface Tensiometer model 6000, which utilizes the maximum bubble pressure method of surface tension analysis. Surface tension profiles of surfactants in deionized water at 25° C. were measured and plotted in dynes/cm on semilog paper.

Ross-Miles Foam Height Test (ASTM D1173-53; SAPM No. 009-1-01)

Ross-Miles foam height measurements were taken at 25° C. Surfactants and cleaner formulations were measured at 0.1% solids unless noted otherwise. 200 ml of a test solution at the desired concentration were dropped through a cylinder impacted with 50 ml of the same solution. Due to the impacting force, foam was generated and its height measured initially and at 5 minutes.

The Dynamic Foam Test (SAPM No. 018-1-01)

This method was developed to monitor foam generation at room temperature over time. A surfactant solution is pumped through an aspirator straight down into a clear glass cylinder (9.5"×24"). To compare hard surface cleaners with different surfactants added, solutions with a total surfactant concentration of 200 ppm in each case are used. The dilute solution is pumped through 1 inch tubing at a flow rate of 5 ft/sec. The foam height is measured at 1 and 5 minutes after the pump is started.

In the following Examples, the formulations of the present invention are compared to conventional sanitizer formulations with respect to equilibrium and dynamic surface tension, dynamic and Ross-Miles foam height, antimicrobial efficacy, and phase stability at low temperatures.

These examples are intended to illustrate the present invention without limiting its scope.

EXAMPLE 1

Equilibrium Surface Tension

A preferred embodiment of the present invention, a mixture of isododecyldimethylamine oxide and decylisononyldimethylammonium chloride, was compared to a standard disinfectant combination comprising an ADBAC and nonylphenol ethoxylate. These blends were tested in the Sensadyne surface tensiometer, at a quaternary:surfactant ratio of 3:1 and a total concentration of 1000 ppm active species. The equilibrium surface tension values are displayed in Table B:

TABLE A

| | QUATERNARY/AMINE OXIDE RATIO | CONCENTRATE (% ACTIVE) | | USE DILUTION (PPM) |
|---|---|---|---|---|
| | | QUATERNARY | AMINE OXIDE | |
| USEFUL | 10:1–0.1:1 | 1–60 | 1–30 | 10–10,000 |
| PREFERRED | 3:1 | 5–20 | 2–15 | 100–1,000 |

Surfactants and formulations were evaluated using the following Standard Applications Methods (SAPM), which

TABLE B

| QUATERNARY/SURFACTANT | EQUILIBRIUM SURFACE TENSION DYNES/CM |
|---|---|
| Myristylbenzyldimethylammonium chloride/12 mole nonylphenol ethoxylate | 43.3 |
| Decylisononyldimethylammonium chloride/Isododecyldimethylamine oxide | 32.7 |

The unique blend of the present invention provides markedly superior surface tension reduction compared to a standard disinfectant/cleaner. It therefore provides enhanced wetting and surface coverage for the formulation at use dilution levels.

EXAMPLE 2

Dynamic Surface Tension

The formulations of Example 1 were evaluated for their dynamic surface tension properties, which are shown in Table C.

TABLE C

| QUATERNARY/SURFACTANT | DYNAMIC SURFACE TENSION, DYNE/CM | | |
|---|---|---|---|
| | 1 bps* | 3 bps | 6 bps |
| Myristylbenzyldimethylammonium chloride/12 mole nonylphenol ethoxylate | 41.8 | 44.4 | 51.8 |
| Decylisononyldimethylammonium chloride/Isododecyldimethylamine oxide | 33.1 | 36.1 | 38.1 |

*bps = bubble per second

The formulation of the present invention has significantly lower surface tension and substantially less overall change in the surface tension than does a typical quaternary/surfactant system, indicating better performance under dynamic (e.g., real world) use conditions.

EXAMPLE 3

Ross-Miles Foaming

Table D compares the Ross-Miles foam heights generated by six quaternary/surfactant combinations, each present at a 3:1 ratio of quaternary ammonium compound to surfactant and at a total concentration of 200 ppm.

TABLE D

| | ROSS-MILES FOAM HEIGHT, mm | |
|---|---|---|
| QUATERNARY/SURFACTANT | INITIAL | 5 MINS |
| Myristyldimethylbenzylammonium chloride/12 mole nonylphenol ethoxylate | 113 | 107 |
| Didecyldimethylammonium chloride/ 12 mole nonylphenol ethoxylate | 120 | 117 |
| Decylisononyldimethylammonium chloride/12 mole nonylphenol ethoxylate | 109 | 41 |
| Didecyldimethylammonium chloride/ dodecyldimethylamine oxide | 117 | 115 |

TABLE D-continued

| | ROSS-MILES FOAM HEIGHT, mm | |
|---|---|---|
| QUATERNARY/SURFACTANT | INITIAL | 5 MINS |
| Decylisononyldimethylammonium chloride/isododecyldimethylamine oxide | 98 | 4 |
| Diisodecyldimethylammonium chloride/ isododecyldimethylamine oxide | 80 | 12 |

A standard mixture of myristyldimethylbenzylammonium chloride and 12-mole nonylphenol ethoxylate produces a high, stable foam. This is also observed when the ADBAC is replaced by didecyldimethylammonium chloride or decylisononyldimethylammonium chloride. The blend of didecyldimethylammonium chloride with the low foaming isododecyldimethylamine oxide still produces high and stable foam.

In contrast, a blend of decylisononyldimethylammonium chloride and isododecyldimethylamine oxide displays not only lower foam initially, but also exhibits dramatically lower foam after 5 minutes. The rapid and almost complete disappearance of foam in this formulation makes it particularly preferred for use in CIP and other I&I applications. Similar low and quick breaking foam was seen when another low foaming quaternary, diisodecyldimethylammonium chloride, was blended with isododecylidmethylamine oxide.

EXAMPLE 4

Dynamic Foaming

The formulations of Example 3 were tested for their foam-generating properties using the dynamic foam test, the results of which are shown in Table E.

TABLE E

| QUATERNARY/SURFACTANT | DYNAMIC FOAM HEIGHT, IN | |
|---|---|---|
| | 1 min | 5 min |
| Myristyldimethylbenzylammonium chloride/12 mole nonylphenol ethoxylate | 7.0 | >9 |
| Didecyldimethylammonium chloride/ 12 mole nonylphenol ethoxylate | >9 | >9 |
| Decylisononyldimethylammonium chloride/12 mole nonylphenol ethoxylate | 8.0 | >9 |
| Didecyldimethylammonium chloride/ dodecyldimethylamine oxide | >9 | >9 |
| Decylisononyldimethylammonium chloride/isododecyldimethylamine oxide | 3.0 | 4.0 |
| Diisodecyldimethylammonium chloride/ isododecyldimethylamine oxide | 2.0 | 2.8 |

The quaternary ammonium/amine oxide blends of the present invention are clearly superior to the other tested formulations with respect to dynamic foaming.

EXAMPLE 5

Antimicrobial Evaluation

Since the primary purpose of a sanitizer or disinfectant cleaner is to reduce or destroy pathogenic bacteria, fungi or viruses, its antimicrobial efficacy needs to be demonstrated. Listed below are two prototype disinfectant cleaner formulations. Formula A is a traditional formulation registered with the EPA, and Formula B is a low foaming formulation in accordance with the present invention.

| | Formula A | Formula B |
|---|---|---|
| Didecyl DMAC, 80% act. | 4.8 | — |
| Decylisononyl DMAC, 80% act. | — | 4.8 |
| Dodecyldimethylamine oxide, 30% act. | 5.0 | — |
| Isododecyldimethylamine oxide, 30% act. | — | 5.0 |
| EDTA Acid | 0.75 | 0.75 |
| NaOH pellet | 0.33 | 0.33 |
| Water and Dye & Fragrance | 89.12 | 89.12 |
| TOTAL | 100.0 | 100.0 |

These compositions are homogeneous, highly stable against phase separation in storage, and can be readily diluted with up to a hundred-fold of water to give disinfectant/sanitizer solutions useful for a wide variety of applications. Table F shows the experimental conditions and results for a typical test.

TABLE F

| | AOAC USE DILUTION TEST | |
|---|---|---|
| Microorganism: | Salmonella choleraesuis ATCC #10708 and Staphylococcus aureus ATCC #6538 | |
| Water Hardness: | 400 ppm | |
| Soil: | 5% serum | |
| Dilution Ratio: | 1:64 | |
| Results: | No. of growth per 10 tubes | |
| | S. CHOLERAESUIS | S. AUREUS |
| FORMULA A | 0/10 | 0/10 |
| FORMULA B | 0/10 | 0/10 |

When tested against *Salmonella choleraesuis* and *Staphylococcus aureus* by the AOAC Use Dilution Test, a test protocol accepted by EPA, no bacterial growth was seen in either the traditional formulation or the low foam formulation.

EXAMPLE 6

Phase Stability Testing

An important feature of any disinfectant cleaner/sanitizer is its phase stability at various temperature conditions ranging from −15° C. to 50° C. For an aqueous based system, a clear one-phase solution is necessary from 0° C. to 50° C.; freezing at subzero temperatures is tolerated only if the product thaws to a clear one-phase solution when allowed to equilibrate at a higher ambient temperature. However, it would be much more advantageous if a system is entirely non-freezing in this temperature range, which would allow its use in very cold environments. Table G compares the phase stability of a conventional formulation with that of the instant invention:

TABLE G

| | FORMULA A | FORMULA B |
|---|---|---|
| Didecyl DAC, 80% act. | 33.62 | — |
| Decylisononyldimethylammonium chloride, 80% act. | — | 33.62 |
| Dodecyldimethylamine oxide, 30% act. | 35.0 | — |
| Isododecyldimethylamine oxide, 30% act. | — | 35.0 |
| Na₃ EDTA | 16.45 | 16.45 |
| Water and Dye & Fragrance | q.s. 100.00 | q.s. 100.00 |
| PHASE STABILITY | | |
| @ Room Temperature | Clear Liquid | Clear Liquid |
| @ −15° C. | Frozen | Clear Liquid |

An unexpectedly beneficial result of the formulations of the present invention is shown above. Formula A, the conventional surfactant/quaternary blend, freezes at −15° C., whereas Formula B, a blend of this invention, remains as a clear liquid at that temperature.

We claim:

1. A sanitizing composition comprising
   a) an amine oxide having the formula:

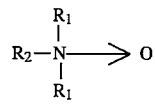

wherein the $R_1$ groups are independently selected from $C_1$–$C_4$ alkyl or alkoxy groups and $R_2$ is a branched chain $C_{11}$–$C_{16}$ alkyl group, and b) a quaternary ammonium compound having the formula:

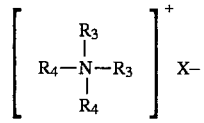

wherein the $R_3$ groups are independently selected from $C_1$–$C_4$ alkyl or alkoxy groups and the $R_4$ groups are $C_8$–$C_{16}$ linear or branched alkyl groups wherein at least one of the $R_4$ groups is a branched $C_8$–$C_{16}$ alkyl group, and X is chloride, bromide, iodide, carbonate or alkylcarboxylate having a $C_1$–$C_{18}$ alkyl radical; the weight ratio of said amine oxide and said quaternary ammonium compound being between about 10:1 and about 0.1:1.

2. The sanitizing composition according to claim 1, wherein said weight ratio is about 1:3.

3. The sanitizing composition according to claim 1, wherein the concentration of said amine oxide is between about 1% and 30% by weight, and the concentration of said quaternary ammonium compound is between about 1% and about 60% by weight, based on the total weight of sanitizing composition.

4. The sanitizing composition according to claim 3, wherein the concentration of said amine oxide is between about 2% and about 15% by weight, and the concentration of said quaternary ammonium compound is between about 5% and about 20% by weight, based on the total weight of sanitizing composition.

5. The sanitizing composition according to claim 1, wherein said amine oxide and said quaternary ammonium compound are each present in at least 50 ppm, based on the total weight of sanitizing composition.

6. The sanitizing composition according to claim 5, wherein the individual concentrations of said amine oxide and said quaternary ammonium compound are each between about 50 ppm and about 1000 ppm, based on the total weight of sanitizing composition.

7. The sanitizing composition according to claim 1, wherein said amine oxide is isododecyldimethylamine oxide.

8. The sanitizing composition according to claim 1, wherein said quaternary ammonium compound is decylisononyldimethylammonium chloride.

9. A sanitizing composition that comprises
   a) isododecyldimethylamine oxide and
   b) decylisononyldimethylammonium chloride,
   wherein the concentration of compound (a) is between about 1% and 3% by weight, the concentration of compound (b) is between about 1% and about 60% by weight, and the weight ratio of (a) to (b) is between about 10:1 to about 0.1:1, said weight percents being based on the total weight of sanitizing composition.

10. A method of preventing the growth of microorganisms which comprises contacting said microorganisms with a sanitizing effective amount of a sanitizing composition comprising
   a) an amine oxide having the formula:

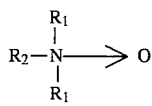

wherein the $R_1$ groups are independently selected from $C_1$–$C_4$ alkyl or alkoxy groups and $R_2$ is a branched chain $C_{11}$–$C_{16}$ alkyl group, and b) a quaternary ammonium compound having the formula:

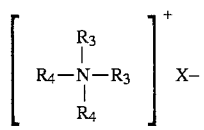

wherein the $R_3$ groups are independently selected from $C_1$–$C_4$ alkyl or alkoxy groups and the $R_4$ groups are $C_8$–$C_{16}$ linear or branched alkyl groups wherein at least one of the $R_4$ groups is a branched $C_8$–$C_{16}$ alkyl group, and X is chloride, bromide, iodide, carbonate, or alkylcarboxylate anion having a $C_1$–$C_{18}$ alkyl radical; the weight ratio of said amine oxide and said quaternary ammonium compound being between about 10:1 and about 0.1:1.

11. The method of claim 10 wherein said amine oxide and said quaternary ammonium compound are each present in at least 50 ppm, based on the total weight of sanitizing composition.

12. The method of claim 10 wherein the concentrations of said amine oxide and said quaternary ammonium compound are each between about 50 ppm and about 1000 ppm, based on the total weight of sanitizing composition.

13. The method of claim 10 wherein said amine oxide is isododecyldimethylamine oxide and said quaternary ammonium compound is decylisononyldimethylammonium chloride.

* * * * *